United States Patent
Noack et al.

(10) Patent No.: US 6,350,779 B1
(45) Date of Patent: Feb. 26, 2002

(54) PIECE-FORM CALCIUM FORMATE

(75) Inventors: Achim Noack, Leichlingen; Hanspeter Baumgartner; Günter Linde, both of Krefeld; Alexander Klausener, Pulheim, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/253,618

(22) Filed: Feb. 19, 1999

(30) Foreign Application Priority Data

Feb. 26, 1998 (DE) .......................... 198 07 996

(51) Int. Cl.$^7$ .......................... A61K 31/28; A61K 9/14; A61K 31/19; A61K 47/00
(52) U.S. Cl. .......................... 514/492; 424/400; 424/489; 424/499; 424/502; 514/597; 514/769; 514/772; 514/777; 514/784; 514/785; 514/788; 514/951
(58) Field of Search .......................... 424/400, 405, 424/408, 409, 464, 489, 499, 500, 501, 502, 600, 682, 19.1; 514/53, 54, 442, 506, 529, 557, 558, 561, 613, 708, 738, 769, 772, 777, 782, 783, 784, 785, 788, 951, 960, 961

(56) References Cited

U.S. PATENT DOCUMENTS

4,741,782 A  *  5/1988  Styron .......................... 588/257
5,686,111 A  *  11/1997  Jalbert .......................... 424/489

FOREIGN PATENT DOCUMENTS

DE         1518686       4/1969
WO         95/24452      9/1995

OTHER PUBLICATIONS

Ullmann's Enzyklopädie der Technischen Chemie [Ullmann's Encyclopedia of Industrial Chemistry], pp 366 & 370(1991).
Ullmann's, 5th edition, vol. A 12, p. 29(1989).

* cited by examiner

Primary Examiner—Jose G. Dees
Assistant Examiner—Frank Choi
(74) Attorney, Agent, or Firm—Joseph C. Gil; Richard E. L. Henderson; Diderico van Eyl

(57) ABSTRACT

Piece-form materials which comprise 5–100% by mass calcium formate and 95–0% by mass additives and have particle sizes of 0.2–5 mm can be prepared from finely crystalline calcium formate and the additives by compression and, if necessary, subsequent comminution and/or fractionation to set the particle size.

19 Claims, No Drawings

PIECE-FORM CALCIUM FORMATE

The invention relates to a process for preparing a piece-form material comprising calcium formate of the formula $Ca(HCOO)_2$, fine-grained calcium formate, with or without the addition of one or more auxiliaries with or without the admixture of one or more further application-promoting components is subjected to a compression and, if appropriate, the resulting material is then fed to a comminution and/or fractionation stage to establish defined particle sizes. The invention further relates to compressed calcium-formate-comprising material having a particle size range of 0.2–5 mm.

Calcium formate is a light crystalline solid, which is used commercially, for example, in the following fields:

- additive in the animal nutrition field (pig, cattle and turkey feed)
- use in the building material industry field (improving the hardening of cement, gypsum and jointing compounds, and also antifreezes for mortar)
- preparation of formic acid
- auxiliary in the leather industry
- aid in the production of high-gloss papers
- treatment of scrubbing waters in flue gas desulphurization
- aid in ensilation.

Calcium formate is produced in various ways, for example by reacting formic acid with calcium hydroxide or by the action of carbon monoxide on calcium hydroxide. Syntheses of this type are described, for example, in Ullmann's Enzyklopädie der Technischen Chemie [Ullmann's Encyclopaedia of Industrial Chemistry] (4th edition), Vol. 7. pp. 366 and 370.

The most important industrial production of calcium formate is carried out in the course of various processes which are known in the literature for preparing polyols, in which calcium formate is obtained as by-product (cf. Ullmann, 5th edition, Vol. A 12, p. 29). The preparation of trimethylolpropane from n-butyraldehyde and formaldehyde using calcium hydroxide as base may be mentioned as an example here. In this process, calcium formate is produced as a coupled product.

Calcium formate may be crystallized, isolated and purified using techniques which are known in principle. Examples of crystallization techniques usable here which may be mentioned by way of example are the evaporative crystallization of aqueous solutions possibly comprising organic material, cooling crystallization and spray-drying. Examples of suitable isolation techniques which may be mentioned by way of example are filtration or centrifugation. Possible purification operations which may be mentioned as examples are redissolution, dispersion, washing and extraction with suitable solvents. If appropriate, one or more suitable drying steps follow such operations or sequences of operations, of which, as suitable processes, hot-air drying, contact drying and vacuum drying may be mentioned as examples.

Common to all these processes is the fact that they deliver polydisperse products which are distinguished by characteristic, more or less broad particle size distributions. In all known industrial processes for preparing calcium formate, significantly high proportions of the total crystals are present in particular in the fine-grained region at particle diameters <0.2 mm. However, for various applications, a product is preferably needed which has a particularly high proportion of coarse-grained particles as far as possible in piece form. The reasons for this can be, for example, certain requirements of occupational hygiene, according to which handling calcium formate having dust contents can pose problems which can only be remedied by additional technical measures which cause economic disadvantages. Other reasons are due to the physical behaviour of fine-grained calcium formate. If, for example, fine-grained calcium formate or calcium formate having high fine-grained contents is introduced into certain commercial coarse-grained structured or shaped animal feed or sililation components, this is frequently associated with considerable mixing problems and with undesirable separations in the further handling of the finished mixture. These effects can restrict the use of calcium formate which is advantageous per se in many fields of application. Although coarse-grained contents can be separated successfully using suitable techniques such as classification, screening and sifting, firstly this causes additional costs, and secondly the fine-grained contents remaining can be supplied to further use only with considerable additional expenditure, in that they are, for example, redissolved, crystallized, isolated and dried and then again fed to the fractionation process. Precisely in processes where calcium formate is only obtained as a by-product, it is frequently not technically or economically expedient to modify the isolation of the preferentially sought-after main product in such as manner that calcium formate arises in fractions which are as coarse-grained as possible.

To convert fine-grained or pulverulent solids into piece-form material, in principle various agglomeration techniques are available whose use can also be considered in principle in the case of crystalline calcium formate. However, experiments which have been carried out to moisten calcium formate, for example by adding small amounts of water in such a manner that larger crystal assemblies are produced on the basis of cohesion of fine particles, generally lead, owing to the hygroscopic properties of dry calcium formate, to the formation of undefined lumps in addition to fine-grained material in unchanged form. Owing to the extremely brittle behaviour of crystalline calcium formate, in addition, shaping processes for compression are not successful by themselves, since the particles produced in these processes have a tendency to crumble readily and as a result unwanted fine-grained contents are generated. Attempts to repress this effect by adding binder immediately fail due to the different application requirements which are made on account of the variety of uses of calcium formate and which frequently do not permit contamination by other additives.

With a view to preparing principally various animal feed products and sililation auxiliaries, there was therefore the object of preparing a calcium-formate-based coarse-grained material as far as possible in piece form which conforms with the requirements of having a particle size distribution which is as narrow as possible and therefore easy to process with a fine grain content which is simultaneously as low as possible. In addition, there was the object of finding a technically feasible economic path for the preparation of such a product. This object is achieved by the product according to the invention and the path according to the invention for its preparation.

It has surprisingly been found that, in contrast to current prejudices and experimental compacting which has proceeded unsuccessfully, piece-form calcium formate having satisfactory application properties can nevertheless be obtained if the heterodisperse fine-grained material which was typically obtained after isolation and purification as by-product of a process for preparing polyols, such as trimethylolethane, trimethylolpropane or pentaerythritol, is subjected to a compression, preferably a compacting, within a defined pressure range. If, for example, pressures are employed below the pressure range which is characteristic of the process according to the invention, piece-form calcium formate can be prepared without the addition of suitable auxiliaries only in comparatively fragile form which has, for example, extremely unfavourable storage properties, such as elevated breakage instability and increased hygroscopicity. If pressures are employed above the pressure range which is characteristic of the process according to the invention, unfortunately, firstly the economic efficiency suffers, secondly an extremely compact material is produced which has a markedly increased, undesirable stability to breakage and, as a result, processing disadvantages, such as lower dissolution rate, increased hardness, higher energy consumption for any downstream fragmentation required, and increased abrasion properties.

The invention relates to a process for preparing a piece-form material which comprises calcium formate in an amount of 5–100% by mass and additives in an amount of 95–0% by mass, based on the total mass of the material and whose particles are in a particle size range of 0.2–5 mm, which is characterized in that finely crystalline calcium formate of a mean particle size below 0.2 mm and additives are subjected to a compression and, if required, the compressed material is subjected to a comminution or fractionation or a combination of the two to set the particle size.

The invention further relates to piece-form material which comprises calcium formate in an amount of 5–100% by mass and additives in an amount of 95–0% by mass, based on the total mass of the material, and whose particles are in a particle size range of 0.2–5 mm.

Starting material for the process according to the invention is fine-grained, pulverulent calcium formate having a mean particle size below 0.2 mm.

The piece-form calcium formate or the piece-form material which can be prepared according to the invention may be produced according to the invention, for example, by means of the fact that the heterodisperse fine-grained material, which was typically produced after isolation and purification as by-product of a process for preparing polyols, such as, trimethylolethane, trimethylolpropane or pentaerythritol, is subjected to a compression, preferably a compacting, within the pressure range specified below. In principle, for this process, use can also be made of calcium formate which was prepared and isolated by another path.

The compression to give the piece-form calcium formate or piece-form material according to the invention can be performed according to the invention by techniques known in principle to those skilled in the art such as compacting, pelleting, granulating, sintering or pressing. Preferably, the compacting technique is employed.

Compacting is performed using apparatuses known to those skilled in the art, preferably using those which are commercially available. The compacting is generally carried out under the conditions according to the invention described below: the roller compression force is 5–100 kN/cm, preferably 10–70 kN/cm, particularly preferably 15–50 kN/cm. The temperature is 5–80° C., preferably 10–40° C., particularly preferably 15–30° C. The peripheral velocity of the roller is 1–100 cm/sec, preferably 3–60 cm/sec, particularly preferably 5–40 cm/sec.

The pulverulent or finely crystalline calcium formate can be introduced into the compacting apparatus in this case, with or without the addition of further additives and/or components, and in principle be introduced using all known conveyor units known to those skilled in the art. Examples which may be mentioned are conveyor belts, screws and vibrating troughs.

If appropriate, a precompression can be carried out using further units known to those skilled in the art, so that a multi-stage compression sequence results as a consequence thereof. A precompression of this type can be achieved, for example, using roller presses, vacuum presses or compression screws.

After carrying out, according to the invention, the compression step for preparing the piece-form calcium formate or material according to the invention, attempts can be made to set a substantially uniform product particle size. For this purpose, a targeted destruction of calcium formate pieces or material pieces is carried out, which pieces are, with respect to their diameter, above a limit to be selected. The said targeted destruction step is performed, for example, using the coarse-grinding technique known to those skilled in the art. Following this process step, with the choice of suitable apparatuses known to those skilled in the art, alternatively in combination with this process step, comminution is carried out with simultaneous removal of sufficiently small particles via a screen apparatus which is variable with respect to its rejection limit. The comminution can be carried out in a simple manner known to those skilled in the art. It can, for example, be carried out using screen granulators, toothed rollers or multiple rollers using friction. Subsequent fractionation is performed, for example, using commercial screening units.

In principle, it is also possible, and is therefore an integral constituent of the invention, in the preparation according to the invention of the piece-form calcium formate to add one or more further substances which, if appropriate, promote the compression operation and/or the application properties and/or the further use of the product according to the invention. Preferably, in this case, the fine-grained calcium formate used is mixed with these further substances before the further compression. As a result, the above described piece-form materials having a calcium formate content deviating from 100% by mass are achieved.

Within the piece-form calcium-formate-comprising materials according to the invention, in the event that, in the course of their preparation according to the invention, one or more additives are admixed, the pure calcium formate content is from 5 to 100% by mass, preferably from 25 to 100% by mass, particularly preferably from 50 to 100% by mass and in particular preferably from 75 to 100% by mass. The contents up to 100% by mass which are missing are then the masses of the additives. Calcium formate and additives are totalled to form the total mass of the piece-form materials.

Additives of this type can be, for example, liquid or solid auxiliaries which, for instance, favourably influence the compacting of the calcium formate to be compressed. In particular, in this case, those substances may be mentioned which are known to those skilled in the art as binders, compacting agents and formulation aids. Auxiliaries of this type which may be mentioned as examples are, water, mineral acids, monohydric, dihydric, trihydric and polyhydric alcohols, such as in particular glycerol, carboxylic acids, carboxylic esters, carboxamides, sulphoxides, fats, fatty acids, fatty alcohols, waxes, tallows and oils of synthetic or natural origin. In addition, possible auxiliaries which may be mentioned are mono-, di-, oligo- and polysaccharides, such as glucose, sucrose, lactose, dextrins, molasses, starch and cellulose, if appropriate except in the pure form, in the form of technical-grade preparations or crude product form.

Substances which may possibly beneficially affect the application properties and/or the further use of the piece-form calcium formate according to the invention are, for instance, fragrance and aroma substances, carbon, such as activated or medical carbon, preservatives and diverse inorganic or organic salts of natural or synthetic origin. Those which can be mentioned as examples are sodium salts, potassium salts, ammonium salts, magnesium salts, calcium salts and iron salts, for instance as chlorides, sulphates, phosphates, silicates, carbonates, hydrogen carbonates, acetates, benzoates and citrates. Other mixing partners which beneficially affect the use of the product according to the invention can be, for example, especially in the animal nutrition field, growth-promoting substances and/or nutritionally active substances. Those which may be mentioned as examples are special feed constituents, vitamins and pharmaceuticals in the broadest sense.

Additives of this type, which beneficially affect the application properties and/or the further use of the piece-form material, can also have properties of binders, compacting agents and formulation aids, so that the latter are no longer required.

The finely crystalline calcium formate being used according to the invention can be mixed with the said further substances in virtually any ways suitable for this and known to those skilled in the art. For example, the mixing can be carried out in stirred vessels, in screws, by pneumatic mixing (pneumatic agitation), by grinding in all mill types suitable for this, by mixing screening, by uniform wetting or by wet agglomeration. In principle, a plurality of the said substances can also be mixed with the calcium formate being used according to the invention and subjected to the subsequent compression and conversion to the material according to the invention comprising piece-form calcium formate.

The said additives and the fine-grained calcium formate being used as starting material according to the invention may be mixed with one another in the abovementioned ratios, limitations arising only due to the physical consistency of the resulting mixtures—they must be firm under the conditions in the subsequent compression and in the further comminution and screening to set the sought-after particle size distribution which may follow.

Example 1

A compactor of type BEPEX CS 25 having fluted smoothing rolls (diameter 22.8 cm, width 6.4 cm, fluting depth 0.3 mm) and screw having a cyclic cone 160 (hydraulic pressure 170 bar, bellows accumulator 110 bar) was charged with cleaned and dried crystalline calcium formate (bulk density 11 $\mu$g/ml) under the conditions specified below:

| Pressure | 230–240 kN |
| --- | --- |
| Roll speed | 15 rpm = approx. 18 cm/sec |
| Screw speed | 30 rpm |
| Feed stream | 310 kg/h |

The piece-form calcium formate produced by compacting was transferred to an ALEXANDER type coarse grinder equipped with a screen of mesh width 1.0 mm. The material thus produced, to separate off the undersized material, was subjected to screening through a Conflux screen (circular vibratory screen, mesh width 323 $\mu$m). The screen oversize (approximately 30% of the total amount) was subjected to a screen analysis. This gave the following values:

| Screen mesh width (mm) | Oversize (% by mass) |
| --- | --- |
| 1.000 | 0.6 |
| 0.500 | 42.6 |
| 0.400 | 23.3 |
| 0.315 | 21.9 |
| <0.315 | 11.6 |

Example 2

A procedure similar to Example 1 was carried out, but under the conditions specified below:

| Pressure | 285–297 kN |
| --- | --- |
| Roll speed | 8 rpm = approx. 9.6 cm/sec |
| Screw speed | 30 rpm |
| Feed stream | 280 kg/h |

The piece-form calcium formate produced by compacting was transferred, as in Example 1, to an ALEXANDER type coarse grinder equipped with a screen of mesh width 1.0 mm. The material thus produced, to separate off the undersized material, was subjected to screening through a Conflux screen (circular vibratory screen, mesh width 323 $\mu$m). The screen analysis of the screen oversize (approximately 30% of the total amount) gave the following values:

| Screen mesh width (mm) | Oversize (% by mass) |
| --- | --- |
| 1.000 | 0.5 |
| 0.500 | 42.5 |
| 0.400 | 22.4 |
| 0.315 | 25.1 |
| <0.315 | 9.5 |

Example 3

A procedure similar to Example 2 was carried out, but using a calcium formate (bulk density 1.111 g/ml) which was first mixed with 1.6% by weight of a 38% strength aqueous sugar solution, using an intensive mixer (Starmix type).

The piece-form calcium formate produced by compacting was transferred, as in Example 2, to an ALEXANDER type coarse grinder, equipped with a screen of mesh width 1.0 mm. The material thus produced, to separate off the undersized material, subjected to screening through a Conflux screen (circular vibratory screen, mesh width 323 $\mu$m). The screen analysis of the screen oversize (approximately 30% of the total amount) gave the following values:

| Screen mesh width (mm) | Oversize (% by mass) |
| --- | --- |
| 1.000 | 0.4 |
| 0.500 | 42.0 |
| 0.400 | 22.9 |
| 0.315 | 25.7 |
| <0.315 | 9.0 |

What is claimed is:
1. A process for preparing a piece-form calcium formate-comprising material comprising compressing (i) a mixture of 5 to 100% by mass of calcium formate having a mean particle size below 0.2 mm and (ii) from 0 to 95% by mass of an additive component of one or more additives, the quantities being based on the total mass of the mixture, thereby forming a piece-form calcium formate-comprising material with particles having a particle size range of 0.2 to 5 mm.

2. The process of claim 1, wherein the process further comprises subjecting the piece-form calcium formate-comprising material to comminution or fractionation or comminution and fractionation.

3. The process according to claim 1, wherein the compressing is carried out in one or more stages by compacting, pelleting, granulating, sintering, or pressing.

4. The process according to claim 1, wherein the compressing is carried out in one or more stages by compacting at a force of 5 to 100 kN/cm and a temperature between 5 and 80° C.

5. The process according to claim 1, wherein the piece-form calcium formate-comprising material is obtained as a by-product of the industrial production of a polyol.

6. The process according to claim 1, wherein the additive component is selected from the group consisting of binders, compacting agents, formulating aids, application promoting substances, and mixtures thereof.

7. The process according to claim 1, wherein the additive component is selected from the group consisting of water, mineral acids, monohydric alcohols, dihydric alcohols, trihydric alcohols, polyhydric alcohols, carboxylic acids, carboxylic esters, carboxamides, sulphoxides, fats, fatty acids, fatty alcohols, waxes, tallows, synthetic oils, natural oils, mono-polysaccharides, di-polysaccharides, oligo-polysaccharides, polysaccharides, fragrances, aromas, carbon, a preservative, a natural or synthetic inorganic or organic salt, growth promoting active substances, and nutritionally active substances, and mixtures thereof.

8. The process according to claim 1, wherein the piece-form calcium formate-comprising material is non-uniform.

9. The process according to claim 1, wherein the piece-form calcium formate-comprising material has a calcium formate content that ranges from 25% to 100% by mass.

10. The process according to claim 9, wherein the piece-form calcium formate-comprising material is non-uniform.

11. The process according to claim 1, wherein the piece-form calcium formate-comprising material has a calcium formate content that ranges from 50% to 100% by mass.

12. The process according to claim 11, wherein the piece-form calcium formate-comprising material is non-uniform.

13. The process according to claim 1, wherein the piece-form calcium formate-comprising material has a calcium formate content that ranges from 75% to 100% by mass.

14. The process according to claim 13, wherein the piece-form calcium formate-comprising material is non-uniform.

15. The process according to claim 1, wherein the process further comprises subjecting separating off undersized material.

16. The process according to claim 15, wherein the undersized material is separated off by screening.

17. A process for preparing a piece-form calcium formate-comprising material comprising (a) compressing (i) a mixture of about 5 to about 100% by mass of calcium formate having a mean particle size below about 0.2 mm and (ii) from 0 to about 95% by mass of one or more additives, the quantities being based on the total mass of the mixture, thereby forming a piece-form calcium formate-comprising material having particles with a particle size range of 0.2 to 5 mm, and (b) subjecting the piece-form calcium formate-comprising material to comminution.

18. A process for preparing a piece-form calcium formate-comprising material comprising:

(a) compressing (i) a mixture of from about 5 to about 100% by mass of calcium formate having a mean particle size below about 0.2 mm and (ii) from 0 to about 95% by mass of one or more additives, the quantities being based on the total mass of the mixture, thereby forming a piece-form calcium formate-comprising material having particles with a particle size range of 0.2 to 5 mm, and (b) subjecting the piece-form calcium formate-comprising material to fractionation by screening.

19. The process of claim 18, wherein the piece-form calcium formate-comprising material is further comminuted by coarse grinding.

* * * * *